US006827947B2

(12) United States Patent
Löfroth et al.

(10) Patent No.: US 6,827,947 B2
(45) Date of Patent: Dec. 7, 2004

(54) FILM COATING

(75) Inventors: Jan-Erik Löfroth, Mölndal (SE); Staffan Schantz, Mölndal (SE); Anders Welin, Mölndal (SE); Lars Johan Pontus de Verdier Hjartstam, Mölndal (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/450,794

(22) PCT Filed: Dec. 18, 2002

(86) PCT No.: PCT/GB02/05739

§ 371 (c)(1),
(2), (4) Date: Jun. 16, 2003

(87) PCT Pub. No.: WO03/051340

PCT Pub. Date: Jun. 26, 2003

(65) Prior Publication Data

US 2004/0030033 A1 Feb. 12, 2004

(30) Foreign Application Priority Data

Dec. 19, 2001 (SE) .............................................. 0104327
Dec. 19, 2001 (SE) .............................................. 0104328

(51) Int. Cl.$^7$ .............................. A61K 9/32; A61K 9/58
(52) U.S. Cl. ........................ 424/497; 424/475; 424/482; 424/490
(58) Field of Search ................................ 424/474, 475, 424/482, 490, 497, 462, 459

(56) References Cited

U.S. PATENT DOCUMENTS

| | | | |
|---|---|---|---|
| 3,341,338 A | 9/1967 | Pater | |
| 3,371,015 A | 2/1968 | Sjogren et al. | |
| 3,775,537 A | 11/1973 | Lehmann et al. | ............. 424/21 |
| 4,330,338 A | * 5/1982 | Banker | ................. 106/162.82 |
| 4,800,087 A | * 1/1989 | Mehta | ....................... 424/497 |
| 4,871,546 A | * 10/1989 | Feltz et al. | ................. 424/482 |
| 4,916,171 A | 4/1990 | Brown et al. | |
| 4,927,640 A | 5/1990 | Dahlinder et al. | |
| 4,957,745 A | 9/1990 | Jonsson et al. | |
| 4,975,283 A | 12/1990 | Patell | ......................... 424/470 |
| 5,246,714 A | 9/1993 | Dahlinder et al. | |
| 5,478,573 A | 12/1995 | Eichel | |
| 5,594,013 A | 1/1997 | Trigger | |
| 5,681,584 A | 10/1997 | Savastano et al. | |
| 5,871,776 A | 2/1999 | Mehta | |
| 6,008,249 A | 12/1999 | Gajdos et al. | |
| 6,046,177 A | 4/2000 | Stella et al. | |
| 6,627,223 B2 | * 9/2003 | Percel et al. | ................ 424/471 |
| 2004/0058001 A1 | 3/2004 | Hölzer et al. | |

FOREIGN PATENT DOCUMENTS

| | | |
|---|---|---|
| EP | 0173928 | 3/1986 |
| EP | 0313845 | 5/1989 |
| EP | 0431877 | 6/1991 |
| EP | 0 621 032 | 10/1994 |
| GB | 0 878 234 | 9/1961 |
| WO | 02058677 | 8/2002 |

OTHER PUBLICATIONS

Röhm Pharma Polymers: Eudragit® sustained–release formulations for oral dosage forms/Eudragit acrylic polymers for controlled release/The complete range/Basic Info 2, pp. 1–20, no date.

Röhm Pharma Polymers: 1. Eudragit® acrylic polymers—International availability and acceptance for use in the manufacture of pharmaceutical dosage forms(05/96), pp. 1–10.

Röhm Pharma Polymers: Specifications and test methods for Eudragit® NE 30 D (Standards Sheet)(01/96), pp. 1–4.

Röhm Pharma Polymers: Specifications and test methods for Eudragit® NE 30 D–55 (Standards Sheet)(01/96), pp. 1–4.

BASF Fine Chemicals: Kollicoat® SR 30 D (Technical Information); Polyvinyl acetate dispersion for sustained–release pharmaceutical formulations (Jun. 1999), pp. 1–14.

BASF Fine Chemicals: Specifications of Kollicoat® SR 30 D (Data Sheet)(Sep. 2003), pp. 1–2.

BASF AG: Fine Chemicals: Pharma Solutions: Excipients: Kollicoat® SR 30 D (2002).

BASF Health and Nutrition: Kollicoat® EMM 30 D (Technical Information); Ethyl acrylate–methyl methacrylate copolymer for sustained–release pharmaceutical formulations (Aug. 1999), pp. 1–11.

BASF Fine Chemicals: Specifications of Kollicoat® EMM 30 D (Data Sheet)(Jul. 2003), pp. 1–2.

BASF AG: Fine Chemicals: Pharma Solutions: Excipients: Kollicoat® EMM 30 D (2002).

Kolter, K. et al., "Kollicoat® SR 30 D—Coatings on Different Drugs", Proceed. Int'l. Symp. Control. Rel. Bioact. Mater., 27(2000) Controlled Release Society, Inc., pp. 425–426.

Sandberg, A. et al., "Design of a New Multiple–Unit Controlled–Release Formulation of Metoprolol—Metoprolol CR", European Journal of Clinical Pharmacology (1988)33 [Suppl] S3–S7.

Ragnarsson, G. et al., "Development of a New Controlled Release Metoprolol Product", Drug Development and Industrial Pharmacy, 13(9–11), 1495–1509(1987).

(List continued on next page.)

Primary Examiner—James M. Spear
(74) Attorney, Agent, or Firm—White & Case LLP

(57) ABSTRACT

A film coating composition suitable for use in coating pharmaceutical formulations to provide modified release comprising a dispersion which includes: a) an acrylic polymer, b) a vinyl acetate polymer, and c) a water-containing liquid. The film coat is useful for the achievement of modified release from pharmaceutical formulations such as tablets, pellets, etc.

50 Claims, No Drawings-

OTHER PUBLICATIONS

Hölzer A.W., "Friction and lubrication in tableting", Industrial Aspects of Pharmaceuticals, Stockholm, Sandell, 1993 ISBN 91–86274465, pp. 153–172.

Z.M. Mathir et al., "In vitro characterization of a controlled-release chlorpheniramine maleate delivery system prepared by the air suspension technique", *J. Microencapsulation*, 1977, vol. 14, No. 6, 743–751.

H–U Petereit et al., "Formulation and process consideration affecting the stability of solid dosage forms formulated with methacrylate copolymers", *European Journal of Pharmaceutics and Biopharmaceutics.*, 47 (1995) 15–25.

M. Wessling et al., "Tackiness of acrylic and cellulosic polymer films used in the coating of solid dosage forms", *European Journal of Pharmaceutics and Biopharmaceutics.*, 47 (1999) 7378.

A.Y. Lin et al., "Study of crystallization of endogenous surfactant in Eudragit NE30D–free films and its influence on drug release properties of controlled–release diphenhydramine HCl pellets coated with Eudragit NE #)D", *AAPS Pharmsci 2001*; 3(2) article 14.

* cited by examiner

FILM COATING

FIELD OF THE INVENTION

The present invention relates to a new film coating. More specifically the present invention relates to a new film coating for the achievement of modified release from pharmaceutical formulations such as tablets, pellets, etc., wherein the film coating may be applied in a substantially aqueous environment. Furthermore, the invention provides a process for the preparation of such a film coating.

BACKGROUND OF THE INVENTION

Oral administration of a drug is the most convenient for the patient. Proper formulations must also meet the requirements of safety and simplicity. Depending on the properties of a drug, and the therapeutic requirements, different approaches must be taken during formulation work to obtain the required delivery profile of the drug. Thus, sparingly soluble drugs to be given once a day require other types of formulations than easily soluble drugs to be taken several times a day. The matter has been discussed extensively in the literature and comprehensive reviews can be found, e.g., Langer and Wise (Eds) "Medical applications of controlled release", vols I and II, CRC Press Inc, Boca Raton, 1984; Robinson and Lee (Eds) "Controlled drug delivery—fundamentals and applications", Marcel Dekker, NY 1987; Bogentoft and Sjögren, in "Towards better safety of drugs and pharmaceutical products" (Ed: Braimer), Elsevier, 1980; Sandberg "Extended-release metoprolol", Thesis, Uppsala University, 1994.

Different formulations have different mechanisms controlling the release of the active substance. In the thesis by Sandberg 1994, extended-release (ER) formulations of different types of drugs are reviewed. It is concluded that in principle two types of ER dosage forms exist: the matrix system where the drug is mixed with the matrix material (often a polymer or a wax); and the drug reservoir system where the drug is formulated into a core (tablet or pellets) surrounded by a polymeric film. The film is then a release rate-controlling barrier determined by, e.g., its permeability, the solubility of the substance, etc.

From a flexibility point of view the formulation of a drug into small discrete units coated with a film has gained much attention. Such formulations show several interesting features, e.g., flexibility in dosage and modification of release properties, different dosage forms can be developed, dose size is adaptable to suit fixed combinations, tablets can be made divisible etc. In a number of studies it was shown that safe, simple, and convenient therapy could be achieved utilising this principle for the drug metoprolol and its salts (Ragnarsson et al, *Drug Develop Ind Pharmacy* 13, 1495 (1987); Sandberg et al, *Eur J Clin Pharmacol* 33, S3 (1988) and S9 (1988); Ragnarsson et al, *Int J Pharmaceutics* 79, 223 (1992); Sandberg et al, Ibid 68, 167 (1991); Sandberg et al, *Pharmaceuticl Res* 10, 28 (1993); Sandberg et al, *Drug Invest* 6, 320 (1993); Sandberg, *Thesis* Uppsala University, 1994). However, the pellets must have good mechanical strength. These pellets are mixed with tablet-forming excipients (Ragnarsson et al, Drug Dev Ind Pharmacy 13, 1495 (1987)) and compressed into tablets. The film coat of a pellet will thus be exposed to external forces in the manufacture of the tablet. If the mechanical strength of the film coat is too low, it may result in core material breakage during the compression process. Breakage can result in a rapid and undesired increase in the release of the drug.

The formulation of metoprolol into pellets according to the above mentioned references utilised a film coating sprayed from a solution of ethyl cellulose and hydroxypropyl methyl cellulose in an organic solvent. However, for environmental reasons it will be necessary in the near future to utilise water based film forming systems for this and other drugs to be formulated as pellet systems. Also, tablet coatings in general utilising organic solvents must for the same reasons be exchanged with water based film forming materials. Thus, much effort has been directed to find suitable water based systems for film coatings in drug delivery systems.

Latex particles in water as the dispersion medium have been known for almost half a century. These particles are polymeric colloidal particles in the 10 to 1000 nm range and have been utilised as film formers, e.g., in paints, in floor coatings, printing inks, adhesives etc. If the particle polymer has a sufficiently low glass transition temperature (Tg) when the water is evaporated, the particles can coalesce to form a film.

Water based film-forming polymer latexes for the pharmaceutical industry have been known since the early eighties when commercial dispersions more frequently appeared on the market (e.g., Aquacoat®, FMC Corp.; Eudragit® NE30D, Röhm Pharma; Kollicoat® EMM30D, BASF AG). Further development has given several other products that have been tested and reported in a number of publications (Petereit and Weisbrod, *Eur J Pharmaceutics and Biopharm* 47, 15 (1999); Petereit et al, Ibid, 41, 219 (1995); Amighi and Moes, *STP Pharma Sci* 7, 141 (1997); Bodmeier and Paeratukul, *Pharm Res* 11, 882 (1994); Ozturk et al, *J Controlled Release* 14, 203 (1990). Goodhart et al, *Pharmaceutical Tech* April, 64 (1984); Bodmeier and Paeratakul *Int J Pharmceutics* 152, 17 (1997); Bodmeier and Paeratakul *Drug Develop Ind Pharmacy* 20, 1517 (1994)).

From these and other studies it can be-concluded that one of the more interesting dispersions, due to the low Tg of the latex polymer, is Eudragit® NE30D, which contains approximately 28.5% w/w particles of the copolymer poly (ethylacrylate-co-methylmethacrylate), and approximately 1.5% w/w of the non-ionic tenside Nonoxynol 100 (a polyoxyethylated nonylphenol) as the stabilizer. A similar dispersion as Eudragit® NE30D is Kollicoat® EMM30D (BASF AG, Ludwigshafen, Germany). However, to obtain best spraying conditions and technical appearance of the film-coated pellets, an anti-sticking agent has to be added to such dispersions as reported by Petereit and Weisbrod 1995. One such agent is a glyceryl monostearate (GMS). Several patents or patent applications utilising these principles exist: Wolff et al, WO 00/13687; Wolff et al, WO 00/13686; Nagy et al, WO 99/42087; Lee et al, WO 99/30685; Eichel et al, U.S. Pat. No. 5,529,790; Eichel U.S. Pat. No. 5,478,573; Chen, U.S. Pat. No. 5,260,068; Petereit et al, EP 403,959; disclose the use of Eudragit® for the (controlled) release of different types of drugs. In those applications when anti-sticking agents have to be used, combinations of surface active molecules and talc or stearates are most common. However, for our purposes these approaches are not attractive since several problems may arise due to, e.g., the combination of non-compatible materials, large amounts of extra dispersion additives, non-reproducibility during manufacturing, etc.

Another dispersion known in the art is the new latex polymer dispersion from BASF, Kollicoat® SR30D. Kollicoat® SR30D is a dispersion which contains approximately 27 % w/w polyvinylacetate, and approximately 2.7% w/w polyvinylpyrrolidone and 0.3% w/w SDS (sodium dodecylsulfate) as stabilizers. However, to be useful for coating application and film formation the polymer dispersion needs a plasticizer such as Triethyl citrate (TEC) (Kolter, K et al., *Proc. Int. Symp. Controlled Release Bioact. Mater.*, 27, 425 (2000)). The use of the plasticizer in a film coating can have a destabilizing effect on the film, probably caused by the migration of small molecules, which can result in the film coating exhibiting a change in its properties with time.

Thus, available latex polymers when used as coating materials present two major problems: (a) sticky pellets may result, due to a low Tg, which then would need extra antisticking agents, and (b) the film may not be strong enough, due to a high Tg, to resist hard compression forces during tablet production, which then would need extra plasticizing agents.

U.S. Pat. No. 4,871,546 discloses tablet coatings comprising polymethyl methacrylate, diethyl phthalate, polyethylene glycol and polyvinyl acetate which are deposited from a solution in an organic liquid, for example methanol or methylene chloride. The polyethylene glycol acts as a plasticizer. This document does not disclose coatings that are applied using aqueous conditions.

EP 431 877 discloses enteric coatings for cimetidine comprising polymer mixtures. Enteric coatings are coatings that are insoluble at low (gastric) pH, but soluble at high (intestinal) pH. This application does not disclose the use of polymers that are water insoluble at both gastric and intestinal pH.

U.S. Pat. No. 4,975,283 discloses enteric coated aspirin. This document does not disclose the use of polymers that are water insoluble at low pH, but soluble at high pH.

U.S. Pat. No. 4,800,087 discloses the combination of Eudragit® L30D and Eudragit®NE30D as a coating to provide an immediate release tablet formulation which has taste-masking properties and is chewable. This document does not disclose the modified release formulations of the present invention.

PURPOSE OF THE INVENTION

The purpose of the present invention is to provide a new film coating system that does not have the above-mentioned problems. Improved properties of the new film coating system are, for example, non-stickiness, high mechanical strength and reproducibility, during processing and a minimal addition of extra additives to the dispersion before the film forming process. Another aspect of the invention is to provide a method of manufacturing coated formulations, for example pellets or tablets, utilising this new film forming system.

SUMMARY OF THE INVENTION

We have now surprisingly found a novel film coating composition which provides a latex dispersion suitable for coating pharmaceutical formulations wherein the film produced serves as a barrier giving close to constant release (zero-order) from the formulation.

The present invention provides a film coating composition suitable for use in coating pharmaceutical formulations to provide modified release comprising a dispersion which comprises:

a) an acrylic polymer,
b) a vinyl acetate polymer,
c) a water-containing liquid, and
d) a stabilizer.

DETAILED DESCRIPTION OF THE INVENTION

In one aspect, the invention provides a film coat covering a pharmaceutical core wherein the core includes a pharmacologically active ingredient and optionally one or more pharmaceutically acceptable excipients. The film coat includes a dispersion which comprises:

a) an acrylic polymer,
b) a vinyl acetate polymer,
c) a water-containing liquid, and
d) a stabilizer, wherein the film coat has been deposited from a water-containing liquid and provides modified release of the pharmacologically active ingredient.

The coating can contain one or more stabilizers. The stabilizer can include one or more small stabilizers (molecular weight less than 15 KD) and\or one or more large stabilizers (molecular weight above 15 KD). In another embodiment the coating contains a stabilizer which has a molecular weight lower than 15 kD and is in a total amount of at least 4% w/w of the acrylic polymer and/or in a total amount of at least 0.5% w/w of the vinyl acetate polymer.

The physical properties of the film produced no processing problems, such as aggregation of particles, and the film exhibited high mechanical strength. Moreover, the film could be made reproducibly.

Further, it has surprisingly been found that if the amount of stabilizer in the film coating is reduced or eliminated the film coating has improved physical properties over time. For example if the stabilizer has a molecular weight lower than 15 kD and is in a total amount of less than 4% w/w of the acrylic polymer and/or in a total amount of less than 0.5% w/w of the vinyl acetate polymer.

In another embodiment the present invention provides a film coating composition suitable for use in coating pharmaceutical formulations to provide modified release comprising a dispersion which comprises:

a) an acrylic polymer,
b) a vinyl acetate polymer, and
c) a water-containing liquid.

The presence of stabilizers for the latex particles in a dispersion creates similar problems as added plasticizers or other additives as the stabilizer can migrate in the film resulting in the film coating exhibiting a change in its properties with time. The above embodiment has the advantage that such migration is reduced or eliminated.

In another aspect, the invention provides a film coat covering a pharmaceutical core wherein the core includes a pharmacologically active ingredient and optionally one or more pharmaceutically acceptable excipients wherein the film coat provides modified release of the pharmacologically active ingredient. The film coat includes a dispersion which includes:

a) an acrylic polymer,
b) a vinyl acetate polymer, and
c) a water-containing liquid, wherein the film coat has been deposited from a water-containing liquid. Suitably the film coat has a thickness in the range of 1 to 100 micrometres, preferably in the range of 5 to 50 micrometres and more preferably in the range of 10 to 30 micrometres. In one embodiment the coating contains one or more stabilizers. The stabilizer can include one or more small stabilizers (molecular weight less than 15 KD) and\or one or more large stabilizers (molecular weight above 15 KD). In another embodiment the coating contains a stabilizer which has a molecular weight lower than 15 kD and which is in a total amount of less than 4% w/w of the acrylic polymer (for example in the range of 0.5 to 4% particularly 1–3%) and/or in a total amount of less than 0.5% w/w of the vinyl acetate polymer (for example in the range of 0.05 to 0.5% particularly 0.1–0.3%).

The pharmacologically active ingredient can be provided in a plurality of beads, optionally containing one or more pharmaceutically acceptable excipients, wherein each of the beads is coated with a film coat as defined above. Such film coated beads may be provided in sachets or formulated as a capsule, for example a hard gelatin capsule, or compressed to form tablets using known methods with the optional addition of other pharmaceutically acceptable additives. Coated beads to be compressed into a tablet are obtained by conventional techniques known to those skilled in the art. Also, during this process suitable other agents can be added. For example, during the tabletting step suitable fillers, e.g., microcrystalline cellulose, talc, sodium stearyl fumarate, etc., can be utilised to give acceptable compression characteristics of the formulation, e.g., hardness of the tablet.

Optionally the beads may contain an insoluble core onto which the active ingredient has been deposited, for example, by spraying. Suitable materials for the inert core are silicon dioxide, glass or plastic resin particles. Suitable types of plastic material are pharmaceutically acceptable plastics such as polypropylene or polyethylene preferably polypropylene. Such insoluble cores have a size diameter in the range of 0.01–2 mm, preferably in the range of 0.05–0.5 mm and more preferably in the range of 0.1–0.3 mm.

In one embodiment, the ductility of the film can be in a range of 500–20000 kJ/m$^3$. In another embodiment the ductility is in the range of 2500–20000 kJ/m$^3$. In yet another embodiment the ductility is in the range of 10000–20000 kJ/m$^3$.

In another aspect, the invention provides a modified release pharmaceutical formulation which includes
 a) a pharmaceutical core comprising a pharmacologically active ingredient and optionally one or more pharmaceutically acceptable excipients, and
 b) a film coat comprising:
  i) an acrylic polymer,
  ii) a vinyl acetate polymer, and
  iii) a stabilizer,
wherein the film coat has been deposited from a water-containing liquid. In one embodiment the coating contains one or more stabilizers. The stabilizer can include one or more small stabilizers (molecular weight less than 15 kD) and\or one or more large stabilizers (molecular weight above 15 kD). In another embodiment the coating contains a stabilizer which has a molecular weight lower than 15 kD and is in a total amount of at least 4% w/w of the acrylic polymer and/or in a total amount of at least 0.5% w/w of the vinyl acetate polymer.

In a preferred aspect, the invention provides a modified release pharmaceutical formulation which includes
 a) a pharmaceutical core comprising a pharmacologically active ingredient and optionally one or more pharmaceutically acceptable excipients, and
 b) a film coat comprising:
  i) an acrylic polymer, and
  ii) a vinyl acetate polymer,
wherein the film coat has been deposited from a water-containing liquid.

The pharmacologically active ingredient can be provided in a plurality of beads, optionally containing one or more pharmaceutically acceptable excipients, wherein each of the beads is coated with a film coat as defined above. Such film coated beads may be provided in sachets or formulated as a capsule, for example a hard gelatin capsule, or compressed to form tablets using known methods with the optional addition of other pharmaceutically acceptable additives. Coated beads to be compressed into a tablet are obtained by conventional techniques known to those skilled in the art. Also, during this process suitable other agents can be added. For example, during the tabletting step suitable fillers, e.g., microcrystalline cellulose, talc, sodium stearyl fumarate, etc., can be utilised to give acceptable compression characteristics of the formulation, e.g., hardness of the tablet. Suitably the beads have a diameter in the range of 0.01–2 mm, preferably in the range of 0.05–1.0 mm and more preferably in the range of 0.1–0.7 mm.

Optionally the beads may contain an insoluble core onto which the active ingredient has been deposited, for example, by spraying. Suitable materials for the inert core are silicon dioxide, glass or plastic resin particles. Suitable types of plastic material are pharmaceutically acceptable plastics such as polypropylene or polyethylene preferably polypropylene. Such insoluble cores have a size diameter in the range of 0.01–2 mm, preferably in the range of 0.05–0.5 mm and more preferably in the range of 0.1–0.3 mm.

In one embodiment, the ductility of the film can be in a range of 500–20000 kJ/m$^3$. In another embodiment the ductility is in the range of 2500–20000 kJ/m$^3$. In yet another embodiment the ductility is in the range of 10000–20000 kJ/m$^3$.

In a more preferred aspect the present invention provides a modified release formulation wherein the pharmacologically active ingredient is released over a long period of time, for example longer than 3 hours in comparison to an immediate release tablet. Preferably the pharmacologically active ingredient is released from the formulation over 10 to 24 hours, for example over 18 to 22 hours.

Preferably the pharmacologically active ingredient has activity in the treatment of cardiovascular diseases. In particular, the pharmacologically active ingredient is a beta-blocking adrenergic agent. The beta-blocking adrenergic agents referred to in this application include but are not limited to the compounds selected from the group consisting of acebutolol, alprenolol, amosulalol, arotinolol, atenolol, befunolol, betaxolol, bevantolol, bisoprolol, bopindolol, bucumolol, bufetolol, bufuralol, bunitrolol, buprandolol, butofilolol, carazolol, carteolol, carvedilol, celiprolol, cetamolol, cloranolol, dilevalol, epanolol, indenolol, labetalol, levobunolol, mepindolol, metipranolol, metoprolol, moprolol, nadolol, nadoxolol, nebivalol, nipradilol, oxprenolol, perbutolol, pindolol, practolol, pronethalol, propranolol, sotalol, sufinalol, talindol, tertatolol, tilisolol, timolol, toliprolol, and xibenolol, and stereoisomers thereof and pharmaceutically acceptable salts or solvates thereof, or solvates of such salts. A preferred beta-blocking adrenergic agent is metoprolol or a pharmaceutically acceptable salt thereof.

In yet another aspect the invention provides a modified release metoprolol formulation including:
 a) a metoprolol core comprising metoprolol or a pharmaceutically acceptable salt thereof and optionally one or more pharmaceutically acceptable excipients; and
 b) a film coat as defined above.

In a preferred aspect the core comprising metoprolol or a pharmaceutically acceptable salt thereof includes a plurality of beads which comprise metoprolol or a pharmaceutically acceptable salt thereof and optionally one or more pharmaceutically acceptable excipients wherein each of the beads is coated with a film-coat as defined above. Preferably, the beads have an inert core as described previously.

Suitable pharmaceutically acceptable salts of metoprolol include the tartrate, succinate, fumarate or benzoate salts and especially the succinate salt. The S-enantiomer of metoprolol or a salt thereof, particularly the benzoate salt or the sorbate salt, may also be used.

The film coating of the invention includes a mixture of an acrylic polymer, a vinyl acetate polymer and optionally one or more stabilizers. Preferably the film coating of the invention includes a mixture of acrylic polymers, e.g. acrylic copolymers with Tg<room temperature and vinyl acetate polymers with a Tg>room temperature.

In one embodiment, the weight ratio of the acrylic polymer (AP) and vinyl acetate polymer (VP) in the film coating is from 0.1/99.9 to 99.9/0.1. Preferably the weight ratio of the AP and the VP in the film coating is from 5/95 to 95/5. More preferably, the weight ratio of AP and VP in the film coating is from 20/80 to 80/20. Most preferably, the weight ratio of AP and VP in the film coating is from 30/70 to 70/30.

The term acrylic polymer as used herein means a water insoluble copolymer (that is a copolymer insoluble both at gastric and at intestinal pH) or blend comprising two or more, of the following monomers: acrylate and methacrylate esters thereof particularly the methyl, ethyl, propyl, and butyl esters , and water insoluble derivatives of acrylic and methacrylic acid. Also water insoluble hydroxylated acrylic and methacrylic esters are included.

One group of preferred acrylic polymers for this use comprises an ethyl acrylate/methyl methacrylate copolymer for example provided by the dispersion Eudragit® NE30D and/or Kollicoat® EMM30D. In this preferred group the ethyl acrylate/methyl methacrylate weight ratio is approximately 2/1.

The term vinyl acetate polymer may include copolymers, or blends thereof, with poly(ethylene), poly(vinyl nitrate), poly(vinyl chloride), poly(vinyl alcohol), poly(vinyl pyrrolidone) or poly(vinylidene fluoride). The vinyl acetate polymer may also include copolymers with; dialkyl maleate, vinyl stearate, and alkyl fumarate. A preferred vinyl acetate polymer is provided by the dispersion Kollicoat® SR30D (BASF AG, Ludwigshafen, Germany).

In a preferred embodiment of the present invention the acrylic polymer and the vinyl acetate polymer are provided by Eudragit® NE30D and/or Kollicoat® EMM30D, and Kollicoat® SR30D in compositions, as film coats or formulations defined previously. The stabilizers provided are then Nonoxynol 100 and/or sodium dodecylsulfate (SDS), and polyvinylpyrrolidone.

The term stabilizer includes any molecule that can ensure and maintain the properties of the latex dispersions. The concentration of the small stabilizers with molecular weights lower than 15 kD amounts to totally less than 4% w/w of the acrylic polymer and/or to totally less than 0.5% w/w of the vinyl acetate polymer, while the concentration of stabilizers with molecular weights higher than 15 kD can have any suitably chosen concentration from 0% w/w and upwards.

Examples of suitable stabilizers include, but are not limited to:

nonionic surfactants, like sorbitan esters (Span series); polysorbates (Tween series); polyoxyethylated glycol monoethers (like the Brij series); polyoxyethylated alkyl phenols (like the Triton series or the Igepal series e.g. Nonoxynol); alkyl glucosides (e.g., dodecylmaltoside); sugar fatty acid esters (e.g., sucrose laurate); saponins; etc: or mixtures thereof;

ampholytic surfactants, like betaines;

anionic surfactants, like sulphated fatty alcohols eg sodium dodecylsulphate SDS; sulphated polyoxyethylated alcohols; others like dioctyl sulphosuccinate; bile salts (e.g., dihydroxy bile salts like sodium deoxycholate, trihydroxy bile salts like sodium glycocholate, etc); fusidates (e.g., sodium dihydrofusidate); etc cationic surfactants, like ammonium compounds;

soaps, fatty acids, and lipids and their salts, like alkanoic acids; (e.g., octanoic acid, oleic acid); monoglycerides (e.g. monolein), phospholipids which are neutral or positively or negatively charged (e.g. dialkyl phosphatidylcholine, dialkyl phosphatidylserine, etc); monoglycerides; phospholipids; cellulose derivatives; polysaccharides; other natural polymers; synthetic polymers( e.g polyvinylpyrrolidone); other substances like shellacs; waxes; nylon; stearates; lipids; paraffin; etc.

Also, combinations of these materials are possible.

Reduction of the concentration or elimination of the stabilizers that might have been provided by the dispersions are carried out by techniques known in the art. These include (M C Wilkinson et al. *Advances in Colloid and Interface Science* 81, 77 (1999)), but are not limited to, dialysis, microfiltration, serum exchange, ultrafiltration, diafiltration, cross-flow microfiltration, centrifugation-decantation, ion-exchange, exchange with resins, activated charcoal cloth, steam stripping, gel filtration and special polymerisation techniques. The reduction of the concentration of stabilizers can be carried out either by applying a cleaning procedure to each dispersion separately before mixing, or by applying a cleaning procedure to the mixed dispersion before spraying the film.

The term plasticizer as used herein means one or more of the following one list: benzyl benzoate, chlorobutanol, dibutyl sebacate, diethyl phthalate, glycerin, mineral oil and lanolin alcohols, petrolatum and lanolin alcohols, polyethylene glycol, propylene glycol, sorbitol, triacetin, triethyl citrate (fom Handbook of Pharmaceutical Excipients, second ed., Eds. A. Wade and P. J. Weller, The Pharmaceutical Press, London 1994). It is a particular advantage of the present invention that the use of plasticizers is kept to a minimum or is eliminated completely since the use of a plasticizer in a film coating can have a destabilizing effect on the film, probably caused by the migration of small molecules, which can result in the film coating exhibiting a change in its properties with time. In yet another aspect the present invention comprises a film coating composition, a film coat or a formulation as described in any previous embodiment characterised in that no plasticizer, as defined above, is present or is present in very low amounts e.g. 0.005 to 0.5% particularly 0.01 to 0.1% by weight.

Suitably the water-containing liquid comprises water and a water miscible organic liquid for example lower alkanols e.g. ethanol, propanol or isopropanol. From a safety point of view it is preferred that the proportion of the organic is kept to a minimum but small amounts are tolerable for example in the range of 0 to 20% by volume. Preferably the liquid is water.

The film-coating composition is particularly suitable for use as an aqueous film-coating composition wherein the film-coat is applied using water as the liquid. When the liquid is water the latex is preferably a poly(ethylacrylate-co-methylmethacrylate) copolymer and a vinyl acetate polymer, for example provided by Eudragit® NE30D (R öhm Pharma) and/or Kollicoat® EMM30D (BASF), and Kollicoat® SR30D (BASF), respectively. This process is particularly advantageous as it negates the need to use environmentally unacceptable organic solvents, some of which also present processing problems due to their flammablility, while also eliminating many of the problems experienced with aqueous coatings described above.

In another aspect the present invention provides processes for the preparation of the film-coating composition. Therefore, there is provided a process for the preparation of a film-coating composition comprising simply mixing together the acrylic polymer dispersion and the vinyl acetate polymer dispersion at a temperature in the range of 0 to 100° C., for example 10 to 100° C., after or before reducing the concentration of stabilizers that might have been provided by the dispersions.

In another embodiment of the process the acrylic polymer dispersion and the vinyl acetate polymer dispersion are mixed at room temperature after or before reducing the concentration of stabilizers that might have been provided by the dispersions.

In yet another embodiment of the process the acrylic polymer, the vinylacetate polymer, the liquid and one or more stabilizers are mixed together at a temperature as defined above after or before reducing the concentration of stabilizers that might have been provided by the dispersions.

Suitably mixing is achieved by methods such as stirring or shaking but other methods of homogenization known to those skilled in the art may be used.

In another aspect the present invention provides a process for film coating a pharmaceutical core wherein a film coating composition as defined above is applied to a core. Preferably the film coating composition is applied by spraying for example in a fluidised bed with top spray or bottom spray techniques. Other coating methods used are coating in standard coating pans with perforated pans, Accela-cota, immersion swords, Glatt, or immersion tubes as described in "Theory and Practice in Industrial Pharmacy" edited by Lachman, published by Lea and Feabiger 1986 $3^{rd}$ edition.

In another aspect the invention provides a process to prepare a film coat as defined above comprising removing the liquid from a film coating composition as defined above. Suitably the liquid is removed by evaporation for example by spray drying for example in a fluidised bed.

In yet another aspect the invention provides a process to prepare a formulation as defined above comprising coating a pharmaceutical core as defined above with a film coating composition as defined above.

In a further aspect the invention provides a process to prepare a formulation in which the pharmacologically active ingredient is provided as a plurality of beads as defined above comprising coating the plurality of beads with a film-coating composition as defined above.

EXAMPLES

The following examples are non-limiting and are given by way of illustration only. It will be appreciated by those skilled in the art that the examples are to be looked upon as guidelines, and the invention is not restricted to the exemplified compositions. A wide range of combinations is possible to give film coatings having the necessary properties required for each specific application.

Example 1

Preparation of Film from Eudragit® NE30D and Kollicoat® SR30D

Films of Kollicoat® SR30D/ and Eudragit® NE30D were prepared by mixing the two dispersions and gentle stirring for two hours at room temperature. The weight fraction of Eudragit® NE30D in the different solutions were: solution A: 20%, solution B: 30%, solution C: 50% and solution D: 70%. Free films (10×10 $cm^2$) of the dispersions were obtained by pouring approximately 10 ml of each dispersions in Teflon moulds. The moulds were then placed in a controlled climate chamber at 25° C./60% relative humidity for drying and film forming during 19 hrs.

Comparative Example 1

Preparation of Films from GMS/PS80/Eudragit® NE30D

Three mixture of GMS, PS80 and Eudragit® NE30D were prepared. Different mixing conditions of GMS and PS80 were used to examine the influence of the stirring rate. Thus, first GMS and PS80 were mixed according to E, F or G below. Then, appropriate amounts of this dispersion were added to Eudragit® NE30D to give the intended compositions. The same amounts of GMS, PS80 and NE30D® were used to prepare solution E, F and G, namely 0.225 g GMS, 0.090 g PS80 and 15.0 g NE30D® which gave dispersions with 1.5% w/w GMS (GMS/particle ratio=5%). This composition was taken from a scientific paper by Petereit and Weisbrod 1995.

E: 1 hour; homogenised at 6000 rpm; 65° C.
F: 20 min; homogenised at 3000 rpm; 65° C.
G: 4 hours; magnet stirring; 65° C.

Free films (10×10 $cm^2$) of the three dispersions were manufactured by pouring approximately 10 ml of each dispersion in Teflon moulds, which were set aside at 25° C., 60% relative humidity for drying and film-formation during 18 hrs.

Example 2

Mechanical Properties

To evaluate the mechanical properties, ductility tests were performed on a Hounsfield H5K-S, a material-testing machine equipped with a 250 N load cell. Pieces of films B, C and G were prepared according to Example 1 (B and C) and Comparative Example 1 (G) and were mounted between the two grips. The length of the samples was 40 mm, with a width of 10 mm and a typical thickness, as measured with a micrometer, of 250 µm. The extension experiment was 4 mm/min and all the experiments were carried out at 23–24° C. and relative humidity of 28–30%. Three or more parallel measurements were made on each film and the ductility was recorded.

Results:

The ductility study is presented in Table 1

TABLE 1

| Ductility of free films | | | |
|---|---|---|---|
| Film | | | |
| | B | C | G |
| Ductility (kJ/$m^3$) | 10693 | 20335 | 6550 |
| SD (%) | 27.6 | 10.2 | 28.6 |

The results show that by mixing the two dispersions, films with higher ductility were gained.

Example 3

Permeability of Free Films

Pieces of the films A–G prepared according to Example 1 (films A, B, C and D) and Comparative Example 1 (films E, F and G) were mounted in diffusion chambers consisting of two chambers, separated by the film segment of interest (Hjärtstam, Thesis, Chalmers University of Technology, Göteborg 1998). A small amount of tritiated water was added to the donor compartment and at specific time intervals a small volume of water was taken from the receiver cell and analysed in a scintillator counter. The water permeability of the film was calculated from the slope of the data of transported amount of labelled water vs. time.

Results:

The water permeability study is presented in Table 2.

TABLE 2

| Permeability of free films | | | | | | | |
|---|---|---|---|---|---|---|---|
| | Film | | | | | | |
| | A | B | C | D | E | F | G |
| Permeability ($10^{-12}$ m$^2$/s) | 22.3 | 19.6 | 5.4 | 2.3 | 30.1 | 40.5 | 51.0 |

It is seen that increased amount of NE30D (A→D) decreased the permeability, while more extensive mixing decreased the permeability of the comparative examples (G→E).

Example 4

Preparation of Coated Metoprolol Succinate Pellets

Metoprolol succinate beads (size fraction 0.40–0.63 mm) were coated with film dispersions A, B, C and D. The dispersions were sprayed onto the beads in a laboratory-scale, fluid-bed Wurster apparatus. The coating conditions were as follows:

| | |
|---|---|
| Bed weight | 200 g |
| Coating solution | ~170 g |
| Spraying rate | 4.6 g/min |
| Atomising air pressure | 2.5 bar |
| Fluidising air flow rate | 35 m$^3$/h |
| Inlet air temp. | 30° C. |
| Outlet air temp. | 20° C. |

The coating pellets were then dried in the fluid-bed, 40° C. (approx. 20 min). During this step the fluidising air flow rate was kept at approximately 20 m$^3$/h and the atomising air pressure at 1 bar.

Results: No problem, e.g. sticking of pellets, was met during the process.

Example 5

Release of Metoprolol from Coated Pellets

The release of metoprolol from about 100 mg pellets according to Example 4 was evaluated in a USP dissolution apparatus No. 2 (rotating paddle) at a speed of 100 rpm. The test medium was 500 ml of phosphate buffer with a pH of 6.8 and ionic strength equal to 0.1 M. The temperature of the bath was set to 37° C. Samples were withdrawn for analysis (absorbance of metoprolol at 274 nm in a 1 cm cell). Amounts of released metoprolol were determined from measurements of the absorbance of a standard metoprolol solution based on the same medium as used in the release experiments.

Results:

TABLE 3

| | Fraction released from pellets | | | | | | | | |
|---|---|---|---|---|---|---|---|---|---|
| | Time/hrs | | | | | | | | |
| | 1 | 2 | 4 | 6 | 8 | 10 | 12 | 16 | 20 |
| (A) % released | 2.2 | 4.4 | 12.2 | 29.4 | 55.8 | 75.1 | 85.9 | — | 99.9 |
| SD (%) | 0 | 0 | 0 | 0 | 0 | 0 | 0 | — | 0 |
| (B) % released | 20.0 | 24.0 | 33.7 | 52.0 | 72.3 | 86.0 | 93.0 | 96.3 | 99.3 |
| SD (%) | 2.4 | 2.4 | 1.8 | 2.0 | 2.1 | 1.0 | 1.0 | 0.58 | 0.73 |
| (C) % released | 2.0 | 4.0 | 16.0 | 41.0 | 66.0 | 83.0 | 91.0 | 97.0 | 99.0 |
| SD (%) | 0 | 0 | 0 | 0 | 0 | 0 | 0 | 0 | 0 |
| (D) % released | 13.0 | 19.3 | 31.3 | 48.0 | 63.3 | 76.3 | 85.0 | 90.3 | 95.3 |
| SD (%) | 1.0 | 0.58 | 0.58 | 0 | 0.58 | 0.58 | 1.0 | 0.58 | 0.58 |

The results from Table 3 show that close to constant release profiles with a modified release up to 20 hours can be achieved.

Example 6

Preparation of Tablets from Coated Metoprolol Pellets

Pellets coated with film dispersion C according to Example 4 were mixed with equal amounts of microcrystalline cellulose, Avicel PH102 in a Turbula mixer T2C (Willy A. Bachofen, Switzerland) for approximately 4 minutes. After addition of 0.15% sodium stearyl fumarate the powder mass was mixed for further 2 minutes. After the mixing was ended the mass was compressed to tablets on an excenter press (Kilian SP300, Germany) using a pressure of approx. 8 kN. The tablet weights were around 200 mg.

Results: No problems were met during the process.

Example 7

Release of Metoprolol from Tablets of Coated Pellets

The release of metoprolol from tablets made according to Example 6 was studied at 37° C. using the USP dissolution apparatus No. 2 (rotating paddle) with stirring rate=100 rpm. The release medium was composed of phosphate buffer with the ionic strength=0.1 M and the pH=6.8. Samples were withdrawn for analysis (absorbance of metoprolol at 274 nm in a 1 cm cell). Amounts of released metoprolol were determined from measurements of the absorbance of a standard metoprolol solution based on the same medium as used in the release experiments.

Results:

The results are presented in Table 4. When comparing the results with the result from pellet release, Table 3 (solution C) it can be seen that there is a very good agreement between these two release profiles and hence it can be concluded that it is possible to compress the pellet into a tablet without losing the modified release profile.

TABLE 4

Fraction released from tablets

| Time/hrs | 1 | 2 | 4 | 6 | 8 | 10 | 12 | 16 | 20 |
|---|---|---|---|---|---|---|---|---|---|
| % released | 0 | 18 | 31 | 47 | 66 | 79 | 88 | 95 | 98 |

Example 8

Cleaning of a Mixed Dispersion with Dialysis

Mixtures of the dispersions Eudragit® NE30D (Röhm Pharma) and Kollicoat® SR30D (BASF) with 30% w/w of Eudragit® NE30D and 70% w/w of Kollicoat® SR30D were dialyzed with Spectra/Por® Dialysis membranes against water (ELGA quality). Due to different dimensions of the membranes when utilizing different molecular weight cut-offs, the dialysis times, amounts of mixed dispersion dialyzed, and the volume of the water were slightly different in the different experiments. The prevailing conditions are given in the results below. The total solid contents of a mixture were determined by drying a known amount of the dialyzed dispersion mixture and weighing. The concentration of the NF100 provided by the NE30D dispersion was determined by UV-spectroscopy at 276 nm. The concentrations of SDS and PVP provided by the Kollicoat® dispersion were determined by elemental analysis (with respect to sulphur=11.1% w/w of SDS and nitrogen=12.6% w/w of PVP) and/or LC-MS (Liquid Cromatography-Mass Spectrometry).
Results:

TABLE I

Analysis of the dialyzed dispersions

| Dialysis number | D1 - 4, 7[a] | D2 - 4, 4[a] |
|---|---|---|
| Molecular cut-off | 14,000 D | 100,000 D |
| Total contents | 21.2% w/w[b] (29.8% w/w)[c] | 17.3% w/w[b] (29.8% w/w)[c] |
| NE 100 concentration | 0.24% w/w[d] (04.5% w/w)[c] | 0.28% w/w[d] (0.45% w/w)[c] |
| SDS concentration | 0.04% w/w[d] (0.14% w/w)[c] | 0.007% w/w[d] (0.14% w/w)[c] |
| PVP concentration | 2.0% w/w[d] (2.2% w/w)[c] | 1.3% w/w[d] (2.2% w/w)[c] |

[a]The numbers indicate the number of changes of the water, and the number of days for dialysis.
[b]Total solid contents after dialysis
[c]Expected in a non-dialyzed mixture of the two dispersions used
[d]Results from elemental analysis or UV, or LC-MS; Corrected for the dilution effect from 29.8% to 21.2 and 17.3% respectively.

It is seen that the amounts of the stabilizers provided by the commercial dispersions Eudragit ® NE30D and Kollicoat ® SR30D were reduced in the final dispersion by the dialysis.

Example 9

Preparation of Free Films from Dialyzed Dispersions

Free films (10×10 cm$^2$) of the dispersions D1 and D2 from Example 8 were obtained by pouring approximately 10 ml of each dispersions in Teflon moulds. The moulds were then placed in a controlled climate chamber at 25° C./60% relative humidity for drying and film forming during 19 hrs. A free film was also made from a non-dialyzed dispersion (D0) for comparison. The composition of the films F0, F1, and F2 made from the dispersions D0, D1, and D2, respectively was calculated from the known concentrations of stabilizers and the total solid contents of the dispersions as presented above in Table I. The results are presented in Table II. Also, the results of the elemental analysis of free films with respect to SDS and PVP are included in Table II.
Results:

TABLE II

Contents of films for permeability experiments.

| | Film | | |
|---|---|---|---|
| | F0 | F1 | F2 |
| NF100 | 1.5% w/w[a] | 0.80% w/w[a] | 0.94% w/w[a] |
| SDS | 0.47% w/w[a] | 0.13% w/w[a] | 0.02% w/w[a] |
| | 1.7% w/w[b] | <0.45% w/w[b] | <0.45% w/w[b] |
| PVP | 8.1% w/w[a] | 6.7% w/w[a] | 4.4% w/w[a] |
| | 6.2% w/w[b] | 5.8% w/w[b] | 3.4% w/w[b] |

[a]Expected from analysis of the dispersions utilized (see Table I)
[b]From elemental analysis It is seen that the amount of the small molecular weight stabilizers NF100 ($M_W \sim 4000$ D) and SDS ($M_W \sim 300$ D) was substantially reduced as compared to the film made from film F0 obtained with a non-dialyzed mixed dispersion. (The SDS elemental analysis was disturbed by the presence of sulphur most probably present in the form of initiators of the polymerisation process.)

Example 10

Permeability of Free Films

Pieces of the films F0, F1 and F2 prepared according to Example 9 were mounted in diffusion cells consisting of two chambers, separated by the film segment of interest (Hjärtstam, Thesis, Chalmers University of Technology, Göteborg 1998). A small amount of tritiated water was added to the donor compartment, and at specific time intervals a small volume of water was taken from the receiver cell and analysed in a scintillator counter. The water permeability of the film was calculated from the slope of the data of transported amount of labelled water vs. time. To evaluate the stability of the film, pieces of the membranes were also kept in a dessicator at RT/60% RH for two weeks before the measurements were carried out.
Results:

TABLE III

Water permeability of films immediately after preparation and after two weeks.

| | Film | | |
|---|---|---|---|
| | F0 | F1 | F2 |
| P (m$^{-12}$ m$^2$/s): New film | 19.6 | 9.8 | 2.6 |
| P (m$^{-12}$ m$^2$/s): After two weeks | 10.4 (−47%) | 7.0 (−29%) | 2.4 (−7%) |

It is seen that the more effective dialysis (higher molecular cut-offs of the dialysis membranes) resulted in a lower permeability of the film. Also, the decrease in permeability of the film over time was less pronounced with films made from the dialyzed dispersions.

Example 11

Preparation of Coated Metoprolol Succinate Pellets

Metoprolol succinate beads (size fraction 0.40–0.63 mm) were coated with film dispersion D2. Before the coating process the dispersion was diluted with water to approximately 14% w/w with respect to total solid contents. The dispersion was sprayed onto the beads in a laboratory-scale, fluid-bed Wurster apparatus. The coating conditions were as follows:

| | |
|---|---|
| Bed weight | 200 g |
| Coating solution | ~340 g |
| Spraying rate | 4.6 g/min |
| Atomising air pressure | 2.5 bar |
| Fluidising air flow rate | 35 m$^3$/h |
| Inlet air temp. | 50° C. |
| Outlet air temp. | 28° C. |

Results: No problems, e g sticking of the pellets, was met during the process.

Example 12

Release of Metoprolol from Coated Pellets

The release of metoprolol from about 100 mg pellets obtained according to Example 11 was evaluated in a USP dissolution apparatus No. 2 (rotating paddle) at a speed of 100 rpm. The test medium was 500 ml of phosphate buffer with a pH of 6.8 and ionic strength equal to 0.1 M. The temperature of the bath was set to 37° C. Samples were withdrawn for analysis (absorbance of metoprolol at 274 nm in a 1 cm cell). Amounts of released metoprolol were determined from measurements of the absorbance of a standard metoprolol solution based on the same medium as used in the release experiments. The experiments were carried out on fresh pellets (0 weeks) and on pellets stored in a dessicator at RT/60% RH for two weeks before the release study.

Results:

TABLE IV

Release of metoprolol from coated pellets.

| | Time (hours) | | | | | | | | |
|---|---|---|---|---|---|---|---|---|---|
| | 1 | 2 | 4 | 6 | 8 | 10 | 12 | 16 | 20 |
| % released - 0 weeks | 12 | 18 | 26 | 34 | 41 | 48 | 54 | 70 | 84 |
| % released - 2 weeks | 9 | 14 | 22 | 31 | 37 | 44 | 51 | 66 | 80 |

It is seen that the release of metoprolol was close to constant over the time interval studied (0–20 hrs). Only a small decrease in the released amounts could be detected between pellets studied immediately and two weeks after preparation, in line with the small decrease in permeability reported in Example 10. Also, the release rate was the same at time "0 weeks" and at "2 weeks".

What is claimed is:

1. A modified release pharmaceutical formulation comprising:
   a) a pharmaceutical core comprising a beta-blocking adrenergic agent as the pharmacologically active ingredient and optionally one or more pharmaceutically acceptable excipients, and
   b) a film coat comprising:
      i) an acrylic polymer, and
      ii) a vinyl acetate polymer,
   wherein the film coat has been deposited from a water-containing liquid.

2. The modified release pharmaceutical formulation according to claim 1 which further comprises iii) a stabilizer.

3. The modified release pharmaceutical formulation according to claim 2, wherein the stabilizer has a molecular weight lower than 15 kD, and wherein the stabilizer is present in a total amount of less than 4% w/w of the acrylic polymer and less than 0.5% w/w/ of the vinyl acetate polymer.

4. A modified release pharmaceutical formulation comprising a beta-blocking adrenergic agent as the pharmacologically active ingredient which is provided in a plurality of beads, wherein the beads optionally contain one or more pharmaceutically acceptable excipients, and wherein each bead is coated with a film coat comprising:
   a) an acrylic polymer, and
   b) a vinyl acetate polymer.

5. The modified release pharmaceutical formulation according to claim 1 or 4, wherein the pharmacologically active ingredient is metoprolol or a pharmaceutically acceptable salt thereof.

6. The modified release pharmaceutical formulation according to claim 5, wherein the metoprolol salt is the tartrate, succinate, fumarate or benzoate salt.

7. A process for the preparation of a formulation according to claim 1 comprising coating the pharmaceutical core with a film coating composition comprising a dispersion which comprises:
   a) an acrylic polymer,
   b) a vinyl acetate polymer and
   c) a water-containing liquid.

8. A process to prepare a formulation as claimed according to claim 4 comprising coating the plurality of beads with a film coating composition comprising a dispersion which comprises:
   a) an acrylic polymer,
   b) a vinyl acetate polymer and
   c) a water-containing liquid.

9. The modified release pharmaceutical formulation according to any one of claims 1–4, wherein the acrylic polymer is an ethylacrylate/methylmethacrylate copolymer.

10. The modified release pharmaceutical formulation according to any one of claims 1–4, wherein the weight ratio of the acrylic polymer and the vinyl acetate polymer is from 20/80 to 80/20.

11. The modified release pharmaceutical formulation according to claim 2, wherein the stabilizer has a molecular weight lower than 15 kD and is present in a total amount of less than 0.5% w/w of the vinyl acetate polymer.

12. The modified release formulation according to claim 4 which further comprises c) a stabilizer.

13. The modified release formulation according to claim 12, wherein the stabilizer has a molecular weight lower than 15 kD, and wherein the stabilizer is present in a total amount of less than 4% w/w of the acrylic polymer and less than 0.5% w/w of the vinyl acetate polymer.

14. The modified release formulation according to claim 12, wherein the stabilizer has a molecular weight lower than 15 kD and is present in a total amount of less than 0.5% w/w of the vinyl acetate polymer.

15. The modified release pharmaceutical formulation according to claim 5, wherein the salt is metoprolol succinate.

16. The modified release pharmaceutical formulation according to claim 5, wherein the salt is metoprolol tartrate.

17. The modified release pharmaceutical formulation according claim 1, wherein the pharmaceutically active agent is released from the formulation over 10 to 24 hours.

18. The modified release pharmaceutical formulation according claim 17, wherein the pharmaceutically active agent is released from the formulation over 18 to 22 hours.

19. The modified release pharmaceutical formulation according claim 4, wherein the pharmaceutically active agent is released from the formulation over 10 to 24 hours.

20. The modified release pharmaceutical formulation according claim 19, wherein the pharmaceutically active agent is released from the formulation over 18 to 22 hours.

21. The modified release pharmaceutical formulation according to any one of claims 17–20, wherein the pharmaceutically active ingredient is metoprolol or a pharmaceutically acceptable salt thereof.

22. The modified release pharmaceutical formulation according to claim 21, wherein the metoprolol salt is the tartrate, succinate, fumarate or benzoate salt.

23. The modified release pharmaceutical formulation according to claim 21, wherein the salt is metoprolol succinate.

24. The modified release pharmaceutical formulation according to claim 21, wherein the salt is metoprolol tartrate.

25. A modified release pharmaceutical formulation comprising:
   a) a pharmaceutical core comprising a beta-blocking adrenergic agent as the pharmacologically active ingredient and optionally one or more pharmaceutically acceptable excipients, and
   b) a film coat comprising:
      i) an acrylic polymer, and
      ii) a vinyl acetate polymer,
wherein the film coat has been deposited from a water-containing liquid, and wherein the pharmaceutically active ingredient is released from the formulation over 10 to 24 hours.

26. The modified release pharmaceutical formulation according to claim 25, wherein the pharmaceutically active ingredient is released from the formulation over 18 to 22 hours.

27. The modified release pharmaceutical formulation according to claim 25 which further comprises iii) a stabilizer.

28. The modified release pharmaceutical formulation according to claim 27, wherein the stabilizer has a molecular weight lower than 15 kD, and wherein the stabilizer is present in a total amount of less than 4% w/w of the acrylic polymer and less than 0.5% w/w/ of the vinyl acetate polymer.

29. A modified release pharmaceutical formulation comprising a beta-blocking adrenergic agent as the pharmacologically active ingredient which is provided in a plurality of beads, wherein the beads optionally contain one or more pharmaceutically acceptable excipients, and wherein each bead is coated with a film coat comprising:
   a) an acrylic polymer, and
   b) a vinyl acetate polymer
wherein the film coat has been deposited from a water-containing liquid, and wherein the pharmaceutically active ingredient is released from the formulation over 10 to 24 hours.

30. The modified release pharmaceutical formulation according to claim 29, wherein the pharmaceutically active ingredient is released from the formulation over 18 to 22 hours.

31. The modified release pharmaceutical formulation according to any one of claims 25–30, wherein the pharmacologically active ingredient is metoprolol or a pharmaceutically acceptable salt thereof.

32. The modified release pharmaceutical formulation according to claim 31, wherein the metoprolol salt is the tartrate, succinate, fumarate or benzoate salt.

33. A process for the preparation of a formulation according to claim 25 comprising coating the pharmaceutical core with a film coating composition comprising a dispersion which comprises:
   a) an acrylic polymer,
   b) a vinyl acetate polymer and
   c) a water-containing liquid.

34. A process to prepare a formulation as claimed according to claim 29, comprising coating the plurality of beads with a film coating composition comprising a dispersion which comprises:
   a) an acrylic polymer,
   b) a vinyl acetate polymer and
   c) a water-containing liquid.

35. The modified release pharmaceutical formulation according to any one of claims 25–30, wherein the acrylic polymer is an ethylacrylate/methylmethacrylate copolymer.

36. The modified release pharmaceutical formulation according to any one of claims 25–30, wherein the weight ratio of the acrylic polymer and the vinyl acetate polymer is from 20/80 to 80/20.

37. The modified release pharmaceutical formulation according to claim 27, wherein the stabilizer has a molecular weight lower than 15 kD and is present in a total amount of less than 0.5% w/w of the vinyl acetate polymer.

38. The modified release formulation according to claim 29 which further comprises c) a stabilizer.

39. The modified release formulation according to claim 38, wherein the stabilizer has a molecular weight lower than 15 kD, and wherein the stabilizer is present in a total amount of less than 4% w/w of the acrylic polymer and less than 0.5% w/w of the vinyl acetate poiymer.

40. The modified release formulation according to claim 38, wherein the stabilizer has a molecular weight lower than 15 kD and is present in a total amount of less than 0.5% w/w of the vinyl acetate polymer.

41. The modified release pharmaceutical formulation according to claim 31, wherein the salt is metoprolol succinate.

42. The modified release pharmaceutical formulation according to claim 31, wherein the salt is metoprolol tartrate.

43. A modified release pharmaceutical formulation comprising:
   a) a pharmaceutical core comprising metoprolol succinate as the pharmacologically active ingredient and optionally one or more pharmaceutically acceptable excipients, and
   b) a film coat comprising:
      i) an acrylic polymer, wherein the acrylic polymer is an ethylacrylate/methylmethacrylate copolymer, and wherein the weight ratio is approximately 2/1, and
      ii) a vinyl acetate polymer, wherein the vinyl acetate polymer is polyvinylacetate,
wherein the film coat has been deposited from water, and wherein the pharmaceutically active ingredient is released from the formulation over 10 to 24 hours.

44. A modified release pharmaceutical formulation comprising:
   a) a pharmaceutical core comprising metoprolol succinate as the pharmacologically active ingredient which is provided in a plurality of beads and optionally one or more pharmaceutically acceptable excipients, and
   b) a film coat comprising:
      i) an acrylic polymer wherein the acrylic polymer is an ethylacrylate/methylmethacrylate copolymer wherein the weight ratio is approximately 2/1, and ii) a vinyl acetate polymer wherein the vinyl acetate polymer is polyvinylacetate, wherein the film coat has been deposited from water, and wherein the pharmaceutically active ingredient is released from the formulation over 10 to 24 hours.

45. The modified release pharmaceutical formulation according to claim 43 or 44, wherein the weight ratio of the acrylic polymer and the vinyl acetate polymer is from 20/80 to 80/20.

46. The modified release pharmaceutical formulation according to any one of claims 1, 4, 25, 29, 43 or 44 in the form of a tablet.

47. The modified release pharmaceutical formulation according to any one of claims 1, 4, 25, or 29 wherein the vinyl acetate polymer is polyvinylacetate.

48. The modified release pharmaceutical formulation according to claim 25 or 29, wherein the acrylic polymer is an ethylacrylate/methylmethacrylate copolymer, and wherein the weight ratio is approximately 2/1.

49. The modified release pharmaceutical formulation according to claim 47 wherein the acrylic polymer is an ethylacrylate/methylmethacrylate copolymer, and wherein the weight ratio is approximately 2/1.

50. The process according to any one of claims 7, 8, 33 or 34 wherein the water-containing liquid is water.

* * * * *